United States Patent
Kwon et al.

(10) Patent No.: US 6,605,697 B1
(45) Date of Patent: Aug. 12, 2003

(54) **MODIFIED *E. COLI* ENTEROTOXIN II SIGNAL PEPTIDE AND A MICROORGANISM EXPRESSING A FUSION PROTEIN OF A SAID PEPTIDE AND A HETEROLOGOUS PROTEIN**

(75) Inventors: Se-Chang Kwon, Seoul (KR); Sung-Youb Jung, Seoul (KR); Hoon Shin, Seoul (KR); Jay-Do Choi, Seoul (KR); Ki-Doo Choi, Seoul (KR); Gwan-Sun Lee, Seoul (KR)

(73) Assignee: Hanmi Pharm. Co., Ltd. (KR)

( * ) Notice: Subject to any disclaimer, the term of this patent is extended or adjusted under 35 U.S.C. 154(b) by 0 days.

(21) Appl. No.: 09/786,569

(22) PCT Filed: Sep. 15, 1999

(86) PCT No.: PCT/KR99/00547

§ 371 (c)(1),
(2), (4) Date: Mar. 7, 2001

(87) PCT Pub. No.: WO00/15661

PCT Pub. Date: Mar. 23, 2000

(30) Foreign Application Priority Data

Sep. 15, 1998 (KR) ............................................. 98-38061

(51) Int. Cl.[7] .......................... C07K 1/00; C07K 14/00; C07K 16/00
(52) U.S. Cl. ........................ 530/300; 530/326; 530/350
(58) Field of Search ................................. 530/300, 326, 530/350

(56) References Cited

PUBLICATIONS

Rudinger et al (*Peptide Hormones* University Park Press, p. 6), 1976.*
Burgess et al (J. of Cell Biology vol. III pp 2129–2138), Nov. 1990.*
Lazar et al (Molecular & Cellular Biology vol. 8(3) pp 1247–1252), Mar. 1988.*
Joblin et al (Molecular Microbiology vol. 5(7) pp 1755–1767), 1991.*

* cited by examiner

Primary Examiner—Mark Navarro
(74) Attorney, Agent, or Firm—Anderson Kill & Olick, PC

(57) ABSTRACT

A heterologous protein is produced by: (i) culturing a microorganism transformed with an expression vector comprising a gene encoding a modified *E. coli* enterotoxin II signal peptide fused with the heterologous protein to produce and secrete the heterologous protein to periplasm, the modified *E. coli* enterotoxin II signal peptide being obtained by replacing at least one of the 2nd, 4th, 5th, 12th, 20th, and 22nd amino acids of *E. coli* enterotoxin II signal peptide of the following amino acid sequence (SEQ ID NO: 1) with another amino acid, with the proviso that at least one of the 2nd and 4th amino acid of the modified peptide is lysine; and (ii) recovering the heterologous protein from the periplasm.

4 Claims, 5 Drawing Sheets

MODIFIED *E. COLI* ENTEROTOXIN II SIGNAL PEPTIDE AND A MICROORGANISM EXPRESSING A FUSION PROTEIN OF A SAID PEPTIDE AND A HETEROLOGOUS PROTEIN

FIELD OF THE INVENTION

The present invention relates to a modified *E. coli* enterotoxin II signal peptide, a gene encoding said peptide, a vector comprising said gene fused with a gene encoding a heterologous protein, a microorganism transformed with said vector, and a process for producing the heterologous protein using said microorganism.

BACKGROUND OF THE INVENTION

Many heterologous proteins have been produced using genetically engineered host microorganisms by an intracellular method or secreting method.

In the intracellular method, a gene encoding a heterologous protein is expressed and accumulated in the cytoplasm of a microorganism. Although this method is known to give a relatively high heterologous protein yield, the expressed heterologous protein is not of a natural active form but methionylated at the N-terminus. Further, the biologically inactive heterologous protein produced by this method often forms insoluble inclusion bodies which must be solubilized and converted into a naturized, active form by a refolding process.

As to the secreting method, a gene encoding a fusion protein of a signal peptide and heterologous protein is expressed in the cytoplasm of a microorganism, and then, the fusion protein is processed by microorganism's signal peptidase to remove the signal peptide while passing through the cytoplasmic membrane. The processed protein is secreted into the periplasm space between the cytoplasmic (inner) membrane and outer membrane of the microorganism. However, this method is known to give a much lower yield of heterologous protein, as compared with the intracellular method. Therefore, there is a need for improving the productivity of the secreting method. In this line, it has been reported that accurate and efficient cleavage of the signal peptide moiety of an expressed fusion protein by signal peptidase is important in enhancing the yield of secreted heterologous protein (Akita, M. et al., *J. Biol. Chem.*, 265, 8164(1990)).

Generally, signal peptides are classified into two groups, hydrophilic signal peptides and hydrophobic signal peptides. A hydrophilic signal peptide is usually composed of 12 to 70 amino acids. A typical hydrophobic signal peptide, e.g., *E. coli* enterotoxin II signal peptide, contains 13 to 30 amino acids, and it is comprised of three regions; an N-terminal hydrophilic region containing one or two basic amino acids; a central hydrophobic region containing about 10 basic amino acids; and a C-terminal hydrophilic region containing amino acids having small side-chains.

As a heterologous protein expressed in the form of a fusion protein with a signal peptide is often degraded rapidly by cytoplasmic proteinase, the yield of secreted heterologous protein decreases as the secretory efficiency of the signal peptide becomes low. Therefore, the yield of secreted heterologous proteins may be enhanced by modifying the signal peptide moiety of fusion proteins expressed in host microorganisms.

Human growth hormone (hGH) is composed of 191 amino acids and has a molecular weight of 21,500 Da. Since a purified form of hGH was first isolated from human pituitary in 1956 (Li and Papkoff, *Science*, 124, 1293 (1956)), there have been made a large number of works on hGH to elucidate, e.g., the effect of hGH on human metabolism (Beck, J. C. et al., *Science*, 125, 884(1957)) and inhibitory activity of hGH on pituitary nanocormia (Raben, M. S., *J. Clin. Endocrinol.*, 18, 901(1958)). Recently, it has been reported that hGH is also effective in the treatment of Turner's syndrome, osteoporosis, vulnus and burn.

As the amount of hGH obtained from human pituitary is limited, there has been an attempt to produce a large amount of hGH in genetically engineered *E. coli* by an intracellular method (Goeddel, D. V. et al., *Nature*, 281, 544 (1979)). However, this method is hampered by the aforementioned problem of producing methionylated hGH which is not suitable for human application. A further attempt to remove methionine from the methionylated hGH using dipeptidyl aminopeptidase I resulted in an unacceptablly low yield of hGH.

Accordingly, the secretory production of natural hGH has been tried. For example, EP Nos 55942, 20147 and 114695 disclose methods for expressing a natural form of hGH and recovering it by secretion. However, the recoverable amount of hGH produced by these methods is only marginal.

EP No. 177,343 discloses a method for producing hGH, which comprises expressing a gene encoding a fusion protein of hGH and alkaline phosphatase or enterotoxin signal peptide, in the presence of an expression inducer, isopropylthio-β-D-galactoside (IPTG), and secreting hGH into periplasm. However, the method gives a low hGH yield and requires the use of the expensive expression inducer, IPTG.

Accordingly, there has been existed a need to develop a new efficient method for producing hGH in a high yield.

SUMMARY OF THE INVENTION

Accordingly, it is an object of the present invention to provide a modified *E. coli* enterotoxin II signal peptide which can be advantageously used in a secreting method of producing a heterologous protein to enhance secretion efficiency.

Another object of the present invention is to provide a gene encoding said peptide.

A further object of the present invention is to provide a vector comprising said gene fused with a gene encoding heterologous protein.

A further object of the present invention is to provide a microorganism transformed with said vector.

A further object of the present invention is to provide a process for producing a hererologous protein using said microorganism.

In accordance with one aspect of the present invention, there is provided a modified *E. coli* enterotoxin II signal peptide (designated MST) characterized in that at least one of the 2nd, 4th, 5th, 12th, 20th and 22nd amino acids of *E. coli* enterotoxin II signal peptide represented by the following amino acid sequence (SEQ ID NO: 1) is replaced by another amino acid, with the proviso that at least one of the 2nd and 4th amino acid of the MST is lysine:

Met Lys Lys Asn Ile Ala Phe Leu Leu Ala Ser Met
                       5                             10

Phe Val Phe Ser Ile Ala Thr Asn Ala Tyr Ala
              15                   20

BRIEF DESCRIPTION OF THE DRAWINGS

The above objects and features of the present invention will become apparent from the following description of preferred embodiments taken in conjunction with the accompanying drawings, in which.

DETAILED DESCRIPTION OF THE INVENTION

Figure 1:
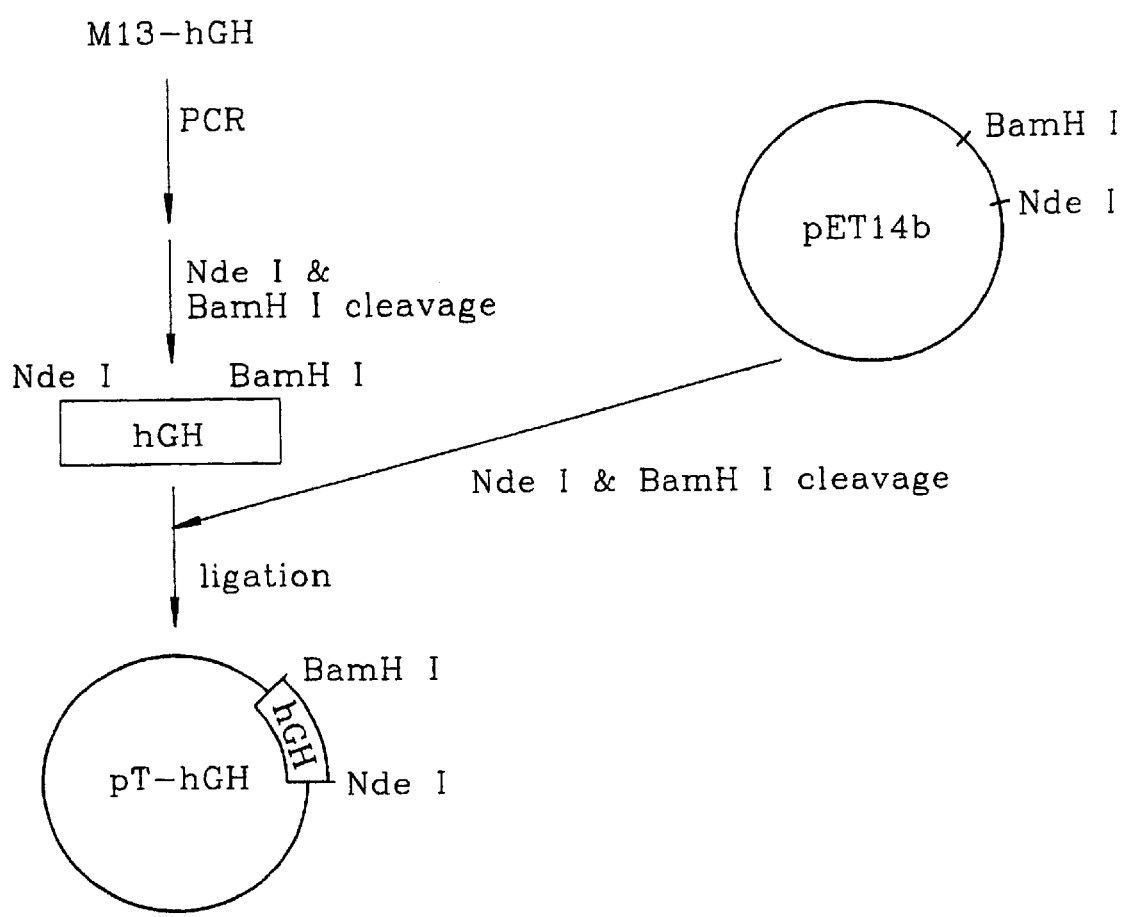
FIG. 1 shows the procedure for constructing vector pT-hGH.

Among the modified E. coli enterotoxin II signal peptides (MSTs) of the present invention, preferred are those, wherein the 2nd amino acid Lys is unsubstituted;

the 4th amino acid Asn is replaced by Ser, Thr, Lys or Gln;

the 5th amino acid Ile is unsubstituted or replaced by Thr or Ser;

the 12th amino acid Met is unsubstituted or replaced by Ala, Gly, Val, Leu or Ile;

the 20th amino acid Asn is unsubstituted or replaced by Ile, Phe, Ala or Val; and the 22nd amino acid Tyr is unsubstituted or replaced by Gln, Asn, Ala or Lys.

Also preferred are those, wherein the 2nd amino acid Lys is replaced by any other amino acid;

the 4th amino acid Asn is replaced by Lys;

the 5th amino acid Ile is replaced by Ser, Thr, Asn, Gln or Arg;

the 12th amino acid Met is unsubstituted or replaced by Ala, Gly, Val, Leu or Ile;

the 20th amino acid Asn is unsubstituted or replaced by Ile, Phe, Ala or Val; and the 22nd amino acid Tyr is unsubstituted or replaced by Gln, Asn, Ala or Lys.

More preferred MSTs are those having one of the following sets of amino acid replacements:

(a) the 4th Asn by Thr and the 22nd Tyr by Gln;

(b) the 4th Asn by Thr, the 20th Asn by Val and the 22nd Tyr by Gln;

(c) the 4th Asn by Lys, the 5th Ile by Thr and the 22nd Tyr by Gln;

(d) the 4th Asn by Ser and the 22nd Tyr by Gln;

(e) the 4th Asn by Ser, the 20th Asn by Val and the 22nd Tyr by Gln;

(f) the 4th Asn by Thr, the 12th Met by Gly, the 20th Asn by Val and the 22nd Tyr by Gln;

(g) the 4th Asn by Thr, the 12th Met by Leu, the 20th Asn by Val and the 22nd Tyr by Gln;

(h) the 4th Asn by Lys, the 5th Ile by Ser and the 22nd is Tyr by Gin;

(i) the 2nd Lys by Val, the 4th Asn by Lys, the 5th Ile by Thr and the 22nd Tyr by Gln; and (j) the 4th Asn by Lys, the 20th Asn by Val and the 22nd Tyr by Gln.

The MST of the present invention may be encoded by a gene comprising a nucleotide sequence deduced from the MST amino acid sequence according to the genetic code. It is known that several different codons encoding a same amino acid may exist due to the codon degeneracy, and, therefore, the MST of the present invention includes all nucleotide sequences deduced from the MST amino acid sequence. Preferably, the MST gene may includes one or more preferred codons of E. coli.

The MST gene may be prepared by mutating one or more nucleotides of native E. coli enterotoxin II signal peptide gene (designated STII gene) using a site-directed mutagenesis (Papworth, C. et al., *Strategies*, 9, 3(1996)). *E. coli* STII gene may be obtained using a conventional method (Sambrook et al., *Molecular Cloninc: A Laboratory Manual*, 2nd ed., Cold Spring Harbor Laboratory Press, USA (1989)). Further, the MST gene may also be synthesized chemically.

The MST of the present invention when fused with a heterologous protein brings about highly efficient secretion of the heterologous protein through the cytoplasmic membrane of a microorganism, e.g., *E. coli*. Accordingly, using an expression vector comprising an MST gene fused with a gene encoding a heterologous protein, a fusion protein of MST and heterologous protein (designated MST/ heterologous protein) can be advantageously expressed in the cytoplasm of *E. coli*, the fusion protein being efficiently processed to remove the MST moiety to release the heterologous protein rapidly into periplasm of *E. coli*. Thus, the use of the inventive MST leads to a greatly enhanced rate of heterologous protein production.

The fusion of an MST gene with a gene encoding a heterologous protein may be conducted according to a conventional ligation method (Sambrook et al., vide supra).

Representative heterologous proteins include human growth hormone (hGH), granulocyte colony stimulating factor (G-CSF), interferon, interleukin, prourokinase, insulin, factor VIII, hirudin, superoxide dismutase and calcitonin, but these do not limit the heterologous proteins which may be used in the present invention. A gene encoding a heterologous protein may be obtained by a conventional method, e.g., cDNA library screening and PCR.

The expression vector of the present invention may further comprise a modified *E. coli* enterotoxin II Shine-Dalgano sequence (modified STII SD sequence) of the following nucleotide sequence (SEQ ID NO: 2) inserted immediately before the initiation codon of the MST gene:

5'-GAGGTGTTTT-3'

The modified STII SD sequence is composed of a 4 nucleotide-long STII SD sequence (GAGG) and a 6 nucleotide-long T-rich sequence. The STII SD sequence of the modified STII SD sequence provides a very strong ribosome binding site, which enhances expression level in the absence of an expression inducer, e.g., isopropylthio-β-D-galactoside (IPTG). The T-rich sequence of the modified STII SD sequence plays the role of preventing the formation of secondary structures of mRNA transcribed therefrom, thereby enhancing the expression efficiency. The modified STII SD sequence may be prepared by conventional methods (Sambrook et al., vide supra) , e.g., chemical synthetic method. Further, the SDII SD gene having the following nucleotide sequence (SEQ ID NO: 3) may be subjected to a site-directed mutagenesis to obtain-modified STII SD sequence:

5'-GCTCTAGAGGTTGAGGTGTTTTATGAAAAAGA ATA-3'

The modified STII SD sequence may be inserted in front of the ATG initiation codon of an MST gene, or the STII SD sequence preceding ATG codon of an MST gene may be modified.

Exemplary expression vectors of the present invention includes pT14S1SH-4T22Q, pT14S1SH-4T20V22Q, pT14S1SH-4K5T22Q, pT14S1SH-4S22Q, pT14S1SH-4S20V22Q, pT14S1SH-4T12G20V22Q, pT14S1SH-4T12L20V22Q, pT14SSH-4K5S22Q, pT14SSH-2V4K5T22Q and pT14SSH-4K20V22Q which are prepared in Examples 1 to 10, and the preferred vectors are pT14S1SH-4T22Q and pT14S1SH-4T20V22Q.

The expression vectors of the present invention may be introduced into microorganism, e.g., E. coli, according to a conventional transformation method (Sambrook et al., the supra). Among the transformed microorganism, preferred are transformants E. coli HM10011 and HM10012 which were deposited with Korean Culture Center oYf Microorganisms (KCCM)(Address; Department of Food Engineering, College of Eng., Yonsei University, Sodaemun-gu, Seoul 120-749, Republic of Korea) on Aug. 12, 1998 under accession numbers of KCCM-10137 and KCCM-10138, respectively, in accordance with the terms of the Budapest Treaty on the International Recognition of the Deposit of Microorganism for the Purpose of Patent Procedure.

A heterologous protein may be produced by culturing the transformant microorganism to express the gene encoding MST/heterclogous fusion protein and secrete a heterologous protein to periplasm; and recovering the heterologous protein from the periplasm. The transformant microorganism may be cultured in accordance with a conventional method (Sambrook et al., the supra). The microorganism culture may be centrifuged or filtered to collect microorganism secreting a heterologous protein. The transformed microorganism may be disrupted according to a conventional method (Ausubel, F. M. et al., *Current Protocols in Molecular Biology* (1989)) to obtain a periplasmic solution. For example, the microorganism may be disrupted in a hypotonic solution, e.g., distilled water, by an osmotic shock. Recovery of the heterologous protein in the periplasmic solution may be conducted by a conventional method (Sambrook et al., the supra), e.g., ion exchange chromatography, gel filtration column chromatography or immune column chromatography. For example, hGH may be purified by sequentially conducting DEAE-Separose column chromatograph, Phenyl separose column chromatography and Sephadex G-100 column chromatography.

The heterologous protein produced according to the present invention is of a natural form, not methionylated at the N-terminus, and therefore, it may be used as is in various application.

The following Examples are intended to further illustrate the present invention without limiting its scope.

PREPARATION EXAMPLE 1

Screening Human Growth Hormone cDNA Gene
(Step 1) Construction of Human Pituitary cDNA Library To 1 g of human pituitary was added 10 ml of guanidine solution (4 M guanidine isocyanate, 50 mM Tris-HCl, pH 7.5, 10 mM EDTA, and 5% 2-mercaptoethanol) and homogenized. The homogenate was centrifuged at 10,000 rpm for 10 min. at 6° C. To the supernatant was added a ⅒ volume of 2% Ether Sarkosyl (Sigma, USA) and the mixture was kept at 65° C. for 2 min. Cesium chloride was added to the resulting solution to a concentration of 0.1 g/ml, and the mixture was centrifuged at 25,000 rpm for 16 hours over 9 ml of a cushion solution(5.7 M CsCl and 0.1 mM EDTA) to obtain RNA precipitate. The precipitate was dissolved in 3 ml of suspension solution (5 mM EDTA, 0.5% Sarkosyl, and 5% mercaptoethanol), and then extracted sequentially with a phenol/chloroform/isoamylalcohol (25:24:1, v/v/v) mixture and chloroform/isoamylalcohol (24:1, v/v) mixture. To the combined extracts were added a ⅒ volume of 3 M sodium acetate and a 2.5 volume of ethanol, and the mixture was centrifuged using conventional method(Sambrook et al., the supra) to obtain RNA precipitate. The RNA precipitate was dissolved in distilled water (D.W.) and kept at 70° C. for 10 min. Lithium chloride was added thereto to a concentration of 0.5 M and then subjected to oligo-dT-cellulose chromatography (Type 3, Collaboratory Research, USA) to isolate poly(A)$^+$ RNA in accordance with the method of Aviv and Leder (Aviv, H and Leder P., *J. Mol. Biol.*, 134, 743 (1972)). The poly(A)$^+$ RNA thus obtained was treated at 65° C. for 5 min., cooled to 0° C., and added immediately thereto was 20 $\mu$l of 5 mM dNTPs, 40 $\mu$l of 5× buffer solution (0.25 M Tris-HCl, pH 8.3, 0.5 M KCl, and 50 mM MgCl$_2$), 10 $\mu$ of 200 mM DTT, 20 $\mu$l of 0.5 mg/ml oligo (dT$_{12-18}$)(Pharmacia Inc., Sweden), 80 $\mu$l of D.W., 10 $\mu$l (10 units) of RNAsin (Promega, USA) and 20 $\mu$l(20 units) of AMV reverse transcriptase (Life Science Inc., USA) After allowing the mixture to react at 42° C. for 90 min., 5 $\mu$l of 0.5 M EDTA(pH 8.0) and 200 $\mu$l of Tris-buffered phenol were added to the reaction mixture, mixed, and centrifuged at 10,000 rpm for 10 min. at room temperature. The supernatant was extracted twice with diethylether and the combined extracts were mixed with 20 $\mu$l of 3 M sodium acetate and 1 ml of 95% ethanol to precipitate single stranded cDNA (ss cDNA)

To synthesize double stranded cDNA (ds cDNA) from the ss cDNA, the ss cDNA precipitate was dissolved in 284 $\mu$l of D.W., and added thereto were 40 $\mu$l of 5 mM NTPs, 80 $\mu$l of 5× second strand (SS) buffer solution (250 mM Tris-HCl (pH 7.2), 450 mM KCl, 15 mM dithiothreitol, 15 mM MgCl$_2$ and, 0.25 mg/ml bovine serum albumin), 12 $\mu$l of 5 mM $\beta$-NAD$^+$, 2 $\mu$l of 3000 Ci/mmol [$\alpha$-$^{32}$P] dCTP, 4 $\mu$l (4 units) of E. coli DNA ligase and 10 $\mu$l (100 units) of E. coli DNA polymerase I. After the mixture was allowed to react at 14° C. for 16 hours, the reaction mixture was subjected to phenol extraction and ethanol precipitation as set forth above to obtain ds cDNA precipitate.

To make a blunt end of ds cDNA, the ds cDNA precipitate was dissolved in 42 $\mu$l of D.W., and added thereto were 5 $\mu$l of dNTPs, 16 $\mu$l of 5×SS buffer solution, 1 $\mu$l of 5 mM $\beta$-NAD$^+$, 4 $\mu$l of RNAase A (2 ug/ml, Biolabs, USA), 4 $\mu$l (4 units) of RNase H, 2 $\mu$l (20 units) of E. coli DNA ligase and 4 $\mu$l (8 units) of T4 DNA polymerase, followed by allowing the mixture to react at 37° C. for 45 min. After completion of the reaction, the reaction mixture was subjected to phenol extraction and ethanol precipitation as set forth above to obtain blunt-ended ds cDNA precipitate.

To protect the EcoRI restriction site of the ds cDNA by methylation, the blunt-ended ds cDNA precipitate was dissolved in 25 $\mu$l of D.W., and added thereto were 27 $\mu$l of 2×methylase buffer (100 mM NaCl, 100 mM Tris-HCl, pH 8.0, and 1 mM EDTA), 1 $\mu$l of 50×SAM solution (1 mg of S-adenosylmethionine in 0.14 ml of sodium acetate (pH 5.2)) and 10 $\mu$l (10 units) of EcoRI methylase (Biolabs, USA) After allowing the mixture to react at 37° C. for 2 hours, the reaction mixture was subjected to phenol extraction and ethanol precipitation as set forth above. The precipitated cDNA was combined with a EcoRI linker (Biolabs, USA) and T4 DNA ligase, and the mixture was reacted at 4° C. for 16 hours to obtain a EcoRI linker-ligated cDNA.

The EcoRI linker-ligated cDNA was treated with EcoRI, and subjected to Sepharose CL-4B column chromatography to remove residual linkers. EcoRI linker-ligated cDNA was inserted at the EcoRI site of $\lambda$gt11 (Amersham, USA). $\lambda$gt11 thus obtained was subjected to in vitro packaging using $\lambda$ in vitro packaging kit. (Amersham Co., USA), and E. coli Y1088 (ATCC37195) was transfected therewith to obtain a human pituitary cDNA library.

(Step 2) Screening Human Growth Hormone cDNA Gene

To screen out human growth hormone clones from the cDNA library prepared in Step 1, plaque hybridization was conducted as follows.

Based on the reported amino acid sequence for the N-terminal of human growth hormone (Liu, W. K., et al, *Biochem. Biophys. Acat.*, 93, 428 (1964); Li, C. H., et al., *J. Amer. Chem. soc.*, 88, 2050 (1966)), 30 nucleotide fragment of mixed sequence oligonucleotide probe represented by following nucleotide sequence were designed and synthesized:

Phe Pro Thr Ile Pro Leu Ser Arg (SEQ ID NO: 4)

5'-TTCCCAACCATTCCCTTATCCAGG-3' (SEQ ID NO: 5)

The primary plaque hybridization was conducted using the mixed sequence oligonucleotide probe in accordance with 35 the method of Benton et al. (Benton, W. E., et al., *Science*, 196, 180 (1977)) to obtain positive clones. These clones were subjected to secondary and tertiary plaque hybridizations to obtain a clone having human growth hormone cDNA gene.

To confirm that the clone has human growth hormone gene, cloned phage DNA was cleaved with EcoRI, and then the DNA fragments were subjected to Southern Blot (Southern, E., *J. Mol. Biol.*, 98, 503 (1975)) using the mixed sequence oligonucleotide probe. Further, a 0.65 kb EcoRI fragment containing human growth hormone gene was insert in the EcoRI site of M13mp18 vector (Pharmacia, USA) to obtain vector M13-hGH. The nucleotide sequence of human growth hormone gene of vector M13-hGH was determined using the dideoxy-mediated chain-termination method (Sanger, F. et al., *Proc. Natl. Acad. Sci. USA*, 74, 5463–5467 (1977)).

PREPARATION EXAMPLE 2

Preparation of A Gene Encoding Mature Human Growth Hormone

To prepare a cDNA gene encoding mature human growth hormone, vector M13-hGH obtained in Step 2 of Preparation Example 1 was subjected to PCR using the following primers S1 and AS1. The sense primer S1 was designed to provide an NdeI restriction site (5'-CATATG-3') upstream from the codon for the first amino acid (phenylalanine), of mature human growth hormone and the antisense primer AS1, to provide a BamHI restriction site (5'-GGATCC-3') downstream from the termination codon thereof.

sense primer S1 (SEQ ID NO: 6):

5'-CCGCATATGTTCCCAACCATTCCC-3' antisense primer AS1 (SEQ ID NO: 7):

5'-GCTGGATCCTAGAAGCCACAGCTGC-3'

The amplified human growth hormone gene was cleaved with NdeI and BamHI to obtain a gene encoding mature human growth hormone (designated hGH gene). The hGH gene was inserted at the NdeI/BamHI section of vector pET14b (Movagen, USA) to obtain vector pT-hGH.

FIG. 1 shows the above procedure for constructing vector pT-hGH.

PREPARATION EXAMPLE 3

Construction of Vector Containing a Gene Encoding *E. coli* Enterotoxin II Signal Peptide/ hGH Fusion Protein (Step 1) Cloning *E. coli* Enterotoxin II Signal Peptide Gene To prepare *E. coli* enterotoxin II signal peptide gene, the following pair of complementary oligonucleotides were designed based on the nucleotide sequence of *E. coli* enterotoxin II signal peptide, and synthesized using DNA synthesizer (Model 380B, Applied Biosystem, USA).

sense strand oligonucleotide STII S1 (SEQ ID NO: 8)
5'-TCATGAAAAAGAATATCGCATTTCTTCTTG CATCTATGTTCGTTTTTTCTATTGC TACAAATGCCTACGCGT-3' antisense strand oligonucleotide STII AS1 (SEQ ID NO: 9) 5'-ACGCGTAGGCATTTGTAGCAATAGAAA AAACGAACATAGATGCAAGAAGAAATGC GATATTCTTTTTCATGA-3'

The oligonucleotides were designed to have NcoI and BspHI restriction sites upstream from the initiation codon of *E. coli* enterotoxin II and an MluI restriction site introduced by a silent change at the other end.

Both oligonucleotides were annealed at 95° C. to obtain blunt-ended ds DNA fragments having a nucleotide sequence encoding *E. coli* enterotoxin II signal peptide (STII gene) The STII gene was inserted at the SmaI site of vector pUC19 (Biolabs, USA) to obtain vector pUC19ST.

(Step 2) Preparation of a Gene Encoding STII/hGH Fusion Protein

To prepare a gene encoding STII/hGH fusion protein, vector pT-hGH obtained in Preparation Example 2 was subjected to PCR using primers S2 and AS1 used in Preparation Example 2. The sense primer S2 was designed to provide an MluI restriction site (5'-CATATG-3') upstream from the codon for the first amino acid (phenylalanine) of mature human growth hormone.

sense primer S2(SEQ ID NO: 10) 5'-GCGACGCGTTCCCAACCATTCCCTTATCC-3'

The amplified DNA fragments were cleaved with MluI and BamHI, and then inserted at the MluI/BamHI section of pUC19ST obtained in Step 2. Vector pUC19SH thus obtained contained a gene encoding an STII/hGH fusion protein (designated STII-hGH gene).

Figure 2:
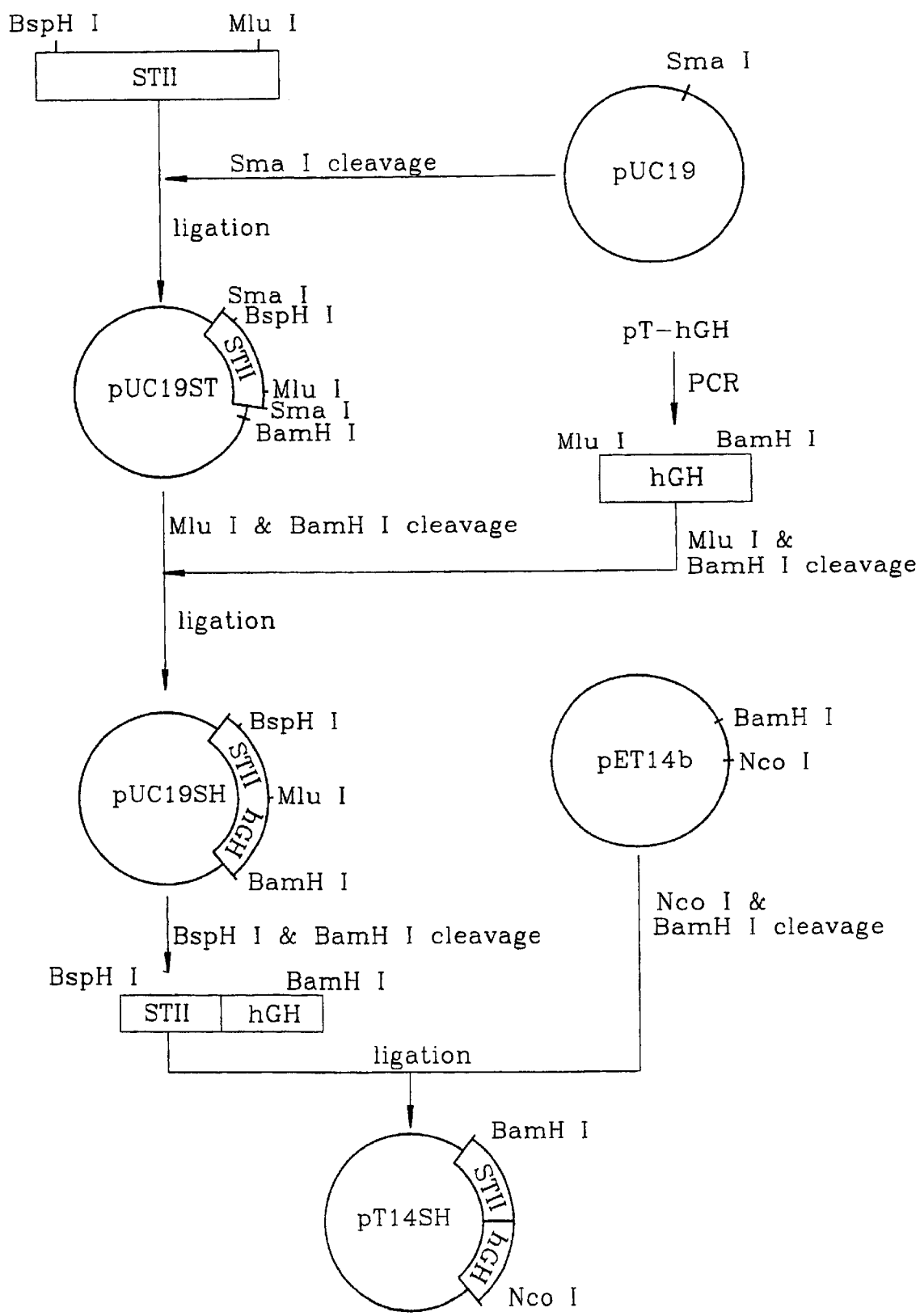
FIG. 2 depicts the procedure for constructing vectors pUC19ST and pUC19SH.

FIG. 2 depicts the above procedure for constructing vectors pUC19ST and pUC19SH.

(Step 3) Addition of *E. coli* Enterotoxin II Shine-Dalgarno Sequence to STII-hGH Gene Vector pUC19SH obtained in Step 2 was cleaved with BspHI and BamHI to obtain a 640 bp STII-hGH fragment, which was inserted at the NcoI/BamHI section of vector pET14b (Novagen, USA) to obtain vector pT14SH.

Vector pT14SH was subjected to PCR using primers S3 and AS3. The sense primer S3 was designed to provide an *E. coli* enterotoxin II Shine-Dalgano sequence (designated STII SD sequence) and an XbaI restriction site, and the antisense primer AS3, to provide a BamHI restriction site downstream from the termination codon of mature hGH to obtain a DNA fragment (STII SD-STII-hGH) containing a STII SD and STII-hGH fusion gene.

sense primer S3(SEQ ID NO: 11) 5'-GCTCTAGAG GTTGAGGTGATTTTATGAAAAAGAATA-3' antisense primer AS3(SEQ ID NO: 12) 5'-GGATGC CACGCTGGATCCTAGAAAGCCACAGCTGC-3'

The STII SD-STII-hGH fragment was cleaved with XbaI and BamHI, and then inserted at the XbaI/BamHI section of vector pET14b (Movagen, USA) to obtain vector pT14SSH. *E. coli* BL21 (DE3) (Stratagene, USA) was transformed with vector pT14SSH to obtain a transformant designated *E. coli* HM10010.

Figure 3:
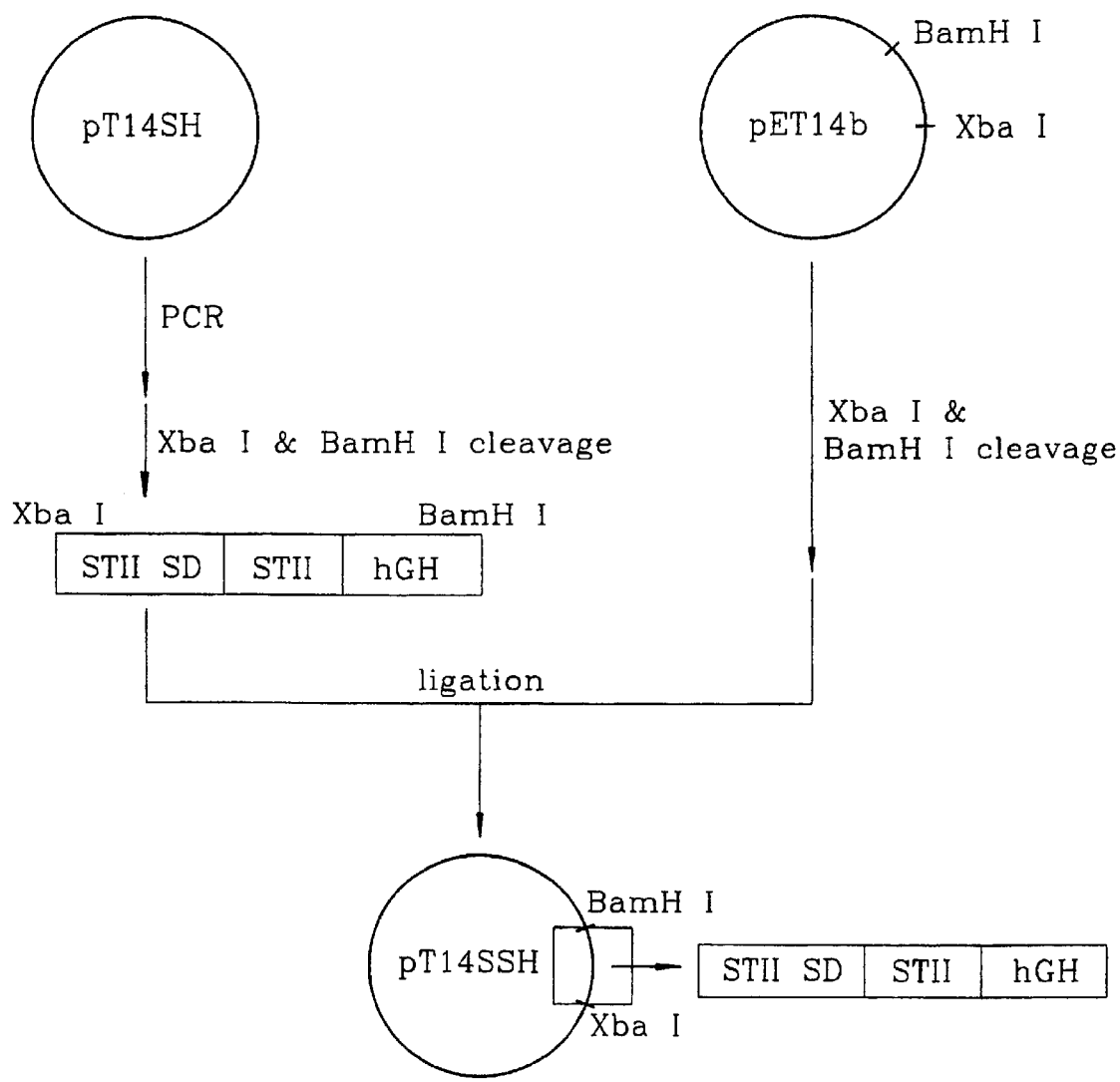
FIG. 3 represents the procedure for constructing vector pT14SSH.

FIG. 3 represents the above procedure for constructing vector pT14SSH.

PREPARATION EXAMPLE 4

Production of hGH Using STII-hGH Gene

To examine the effect of *E. coli* enterotoxin II SD sequence on the production of hGH, *E. coli* BL21 (DE3) transformed with vector pT14SH obtained in Step 3 of Preparation Example 3 and *E. coli* HM10010 obtained also in Step 3 of Preparation Example 3 were cultured in the presence and absence of an expression inducer (IPTG), respectively, in LB medium (1% bacto-tryptone, 0.5% bacto-yeast extract and 1% NaCl) at 37° C. for 24 hours. Each of cultures was centrifuged at 10,000 rpm for 10 min. to precipitate bacterial cell, and the precipitate was suspended in a ¹/₁₀ volume of isotonic solution (20% sucrose, 10 mM Tris-Cl buffer solution containing 1 mM EDTA, pH 7.0). The suspension was allowed to stand at room temperature for 30 min, and then centrifuged at 10,000 rpm for 15 min. to collect bacterial cells. The cells were resuspended in D.W. at 4° C. and centrifuged at 12,000 rpm for 20 min. to obtain a supernatant as a periplasmic solution. The hGH level in the periplasmic solution was assayed in accordance with ELISA method (Kato, K. et al., *J. Immunol.*, 116, 1554(1976)) using an antibody against hGH (Boehringer Mannheim), which was calculated as the amount of hGH produced per 1 l of culture. The results are shown in Table I.

TABLE I

|  | pT14SH |  | pT14SSH |  |
| --- | --- | --- | --- | --- |
| IPTG | − | + | − | + |
| hGH level (mg/l) | 120 | 100 | 330 | 250 |

As can be seen from Table I, vector pT14SSH, which contains the STII SD sequence, produces hGH at a high level, even in the absence of an expression inducer, IPTG.

EXAMPLES 1 TO 10

Examples 1 to 10 describe the construction of vectors each containing a gene encoding an MST/hGH fusion protein according to the present invention, wherein MST stands for modified *E. coli* enterotoxin II signal peptide. The STII gene or STII SD sequence of plasmid pT14SSH obtained in Step 3 of Preparation Example 3 was modified in accordance with a site-directed mutagenesis (Papworth, C. et al., *Strategies*, 9, 3 (1996)), which was conducted by PCR of the plasmid with a sense primer having a modified nucleotide sequence and an antisense primer having a nucleotide sequence complementary to sense primer.

Modified *E. coli* enterotoxin II signal peptides obtained Examples 1 to 10, MSTs (MST1 to MST10), are characterized in Table II together with STII, and the preparative procedure of Examples 1 to 10 are described below.

TABLE II

| Example | MST | 2nd | 4th | 5th | 12th | 20th | 22nd |
| --- | --- | --- | --- | --- | --- | --- | --- |
|  | STII (SEQ ID NO: 1) | Lys | Asn | Ile | Met | Asn | Tyr |
| 1 | MST1 (SEQ ID NO: 13) | Lys | Thr | Ile | Met | Asn | Gln |
| 2 | MST2 (SEQ ID NO: 14) | Lys | Thr | Ile | Met | Val | Gln |
| 3 | MST3 (SEQ ID NO: 15) | Lys | Lys | Thr | Met | Asn | Gln |
| 4 | MST4 (SEQ ID NO: 16) | Lys | Ser | Ile | Met | Asn | Gln |
| 5 | MST5 (SEQ ID NO: 17) | Lys | Ser | Ile | Met | Val | Gln |
| 6 | MST6 (SEQ ID NO: 18) | Lys | Thr | Ile | Gly | Val | Gln |
| 7 | MST7 (SEQ ID NO: 19) | Lys | Thr | Ile | Leu | Val | Gln |
| 8 | MST8 (SEQ ID NO: 20) | Lys | Lys | Ser | Met | Asn | Gln |
| 9 | MST9 (SEQ ID NO: 21) | Val | Lys | Thr | Met | Asn | Gln |
| 10 | MST10 (SEQ ID NO: 22) | Lys | Lys | Ile | Met | Val | Gln |

EXAMPLE 1

Construction of Vector Containing a Gene Encoding MST1/hGH Fusion Protein (Step 1)

Vector pT14SSH obtained in Step 3 of Preparation Example 3 was subjected to PCR using the following complementary primers S4 and AS4 which were designed to substitute Thr codon (ACA) for the 4th codon (ATT) of STII.

sense primer S4(SEQ ID NO: 23): 5'-GGTGTTTTA TGAAAAAGACAATCGCATTTCTTC-3' antisense primer AS4 (SEQ ID NO: 24) 5'-GAAGAA ATGCGATTGTCTTTTTCATAAAACACC-3'

The vector thus obtained was cleaved with XbaI and MluI to obtain a 0.1 kb XbaI/MluI fragment, which was inserted in the XbaI/Mlu I section of vector pT14SSH to obtain vector pT14SSH-4T. Vector pT14SSH-4T contains a gene encoding a modified STII/hGH fusion protein having Thr in place of the 4th amino acid of STII.

(Step 2)

Vector pT14SSH-4T was subjected to PCR using the following complementary primers S5 and AS5 which were designed to substitute Gln codon (CAA) for the 22nd codon (AAT) of STII; to obtain vector pT14SSH-4T22Q.

sense primer S5(SEQ ID NO: 25): 5'-CAAATG CCCAAGCGTTCCCA-3' antisense primer AS5(SEQ ID NO: 26): 5'-TGGGAA CGCTTGGGCATTTG-3'

Vector pT14SSH-4T22Q contained a gene encoding MST1/hGH fusion protein in which the 4th and 22nd amino acids of STII were replaced with Thr and Gln, respectively.

(Step 3)

Vector pT14SSH-4T22Q was subjected to PCR using the following complementary primers S6 and AS6 having the six nucleotide sequences shown below between the STII SD sequence 5'-GAGG-3' and the initiation codon of STII in order to prevent the formation of secondary structures of MRNA transcribed therefrom.

sense primer S6(SEQ ID NO: 27): 5'-TCTAGA GGTTGAGGTGTTTTATGA-3' antisense primer AS6(SEQ ID NO: 28): 5'-TCATAA AACACCTCAACCTCTAGA-3'

Vector pT14S1SH-4T22Q thus obtained contained a modified STII SD sequence and a gene encoding MST1/hGH fusion protein in which the 4th and 22nd amino acids of STII were replaced with Thr and Gln, respectively.

Figure 4:
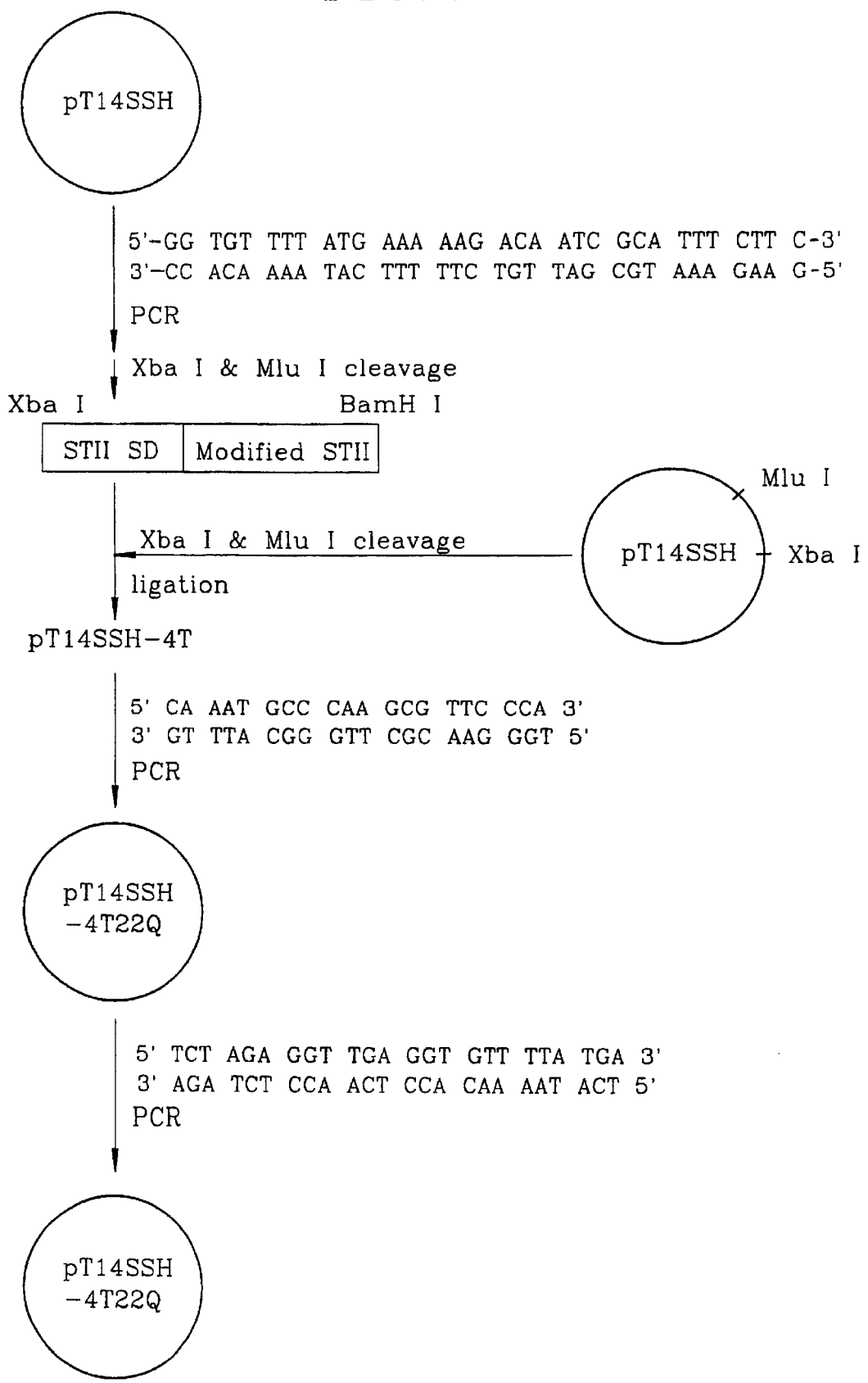
FIG. 4 shows the procedure for constructing vector pT14S1SH.

FIG. 4 shows the above procedure for constructing vector pT14S1SH.

E. coli BL21 (DE3) was transformed with vector pT14S1SH-4T22Q to obtain a transformant designated E. coli HM10011, which was deposited with Korean Culture Center of Microorganisms (KCCM) on Aug. 12, 1998 under accession number of KCCM-10137.

EXAMPLE 2

Construction of Vector Containing a Gene Encoding MST2/hGH Fusion Protein

The procedure of Step 2 of Example 1 was repeated except for using the following complementary primers S7 and AS7 which were designed to substitute Val and Gln codons (GTT and CAA for the 20th and 22nd codons (AAT and TAT) of STII, respectively, to obtain vector pT14SSH-4T20V22Q.

sense primer S7 (SEQ ID NO: 29): 5'-GTTTTTTCT ATTGCTACAGTTGCCCAAGCGTTCCCAACCATT CCC-3' antisense primer AS7(SEQ ID NO: 30): 5'-GGGAAT GGTTGGGAACGCTTGGGCAACTGTAGCAAT AGAAAAAAC-3'

Then, the procedure of Step 3 of Example 1 was repeated except for using vector pT14SSH-4T20V22Q, to obtain vector pT14S1SH-4T20V22Q. Vector pT14S1SH-4V20V22Q contained a modified STII SD sequence and a gene encoding MST3/hGH fusion protein in which the 4th, 20th and 22nd amino acids of STII were replaced with Thy, Val and Gln, respectively.

E. coli BL21 (DE3) was transformed with vector pT14S1SH-4T20V22Q to obtain a transformant designated E. coli HM10012, which was deposited with KCCM on Aug. 12, 1998 under the accession number of KCCM-10138.

EXAMPLE 3

Construction of Vector Containing a Gene Encoding MST3/hGH Fusion Protein

The procedure of Step 1 of Example 1 was repeated except for using the following complementary primers S8 and AS8 was used which were designed to substitute Lys and Thr codons (AAG and ACA) for the 4th and 5th codons (AAT and ATC) of STII, respectively, to obtain vector pT14SSH-4K5T.

sense primer S8(SEQ ID NO: 31): 5'-GAGGTGTTT TATGAAAAAGAAGACAGCATTTCTTC-3' antisense primer AS8(SEQ ID NO: 32): 5'-GAAGAA ATGCTGTCTTCTTTTTCATAAAACACCTC-3'

Using vector pT14SSH-4K5T was used, the procedure of Step 2 of Example 1 was repeated to obtain vector pT14SSH-4K5T22Q.

Then, the procedure of Step 3 of Example 1 was repeated using vector pT14SSH-4K5T22Q, to obtain vector pT14S1SH-4K5T22Q. Vector pT14S1SH-4K5T22Q contained a modified STII SD sequence and a gene encoding MST3/hGH fusion protein in which the 4th, 5th and 22nd amino acids of STII were replaced with Lys, Thr and Gln, respectively.

E. coli BL21(DE3) was transformed with vector pT14S1SH-4K5T22Q to obtain a transformant designated E. coli HM10013.

EXAMPLE 4

Construction of Vector Containing a Gene Encoding MST4/hGH Fusion Protein

The procedure of Step 1 of Example 1 was repeated except for using the following complementary primers S9 and AS9 which were designed to substitute Ser codon (TCT) for the 4th codon (AAT) of STII, to obtain vector pT14SSH-4S.

sense primer S9(SEQ ID NO: 33) 5'-GAGGTGTTT TATGAAAAAGTCTATCGCATTTCTTC-3' antisene primer AS9(SEQ ID NO: 34) 5'-GAAGAA ATGCGATAGACTTTTTCATAAAACACCTC-3'

Using vector pT14SSH-4S, the procedure of Step 2 of Example 1 was repeated to obtain vector pT14SSH-4S22Q.

Then, the procedure of Step 3 of Example 1 was repeated using vector pT14SSH-4S22Q, to obtain vector pT14S1SH-4S22Q. Vector pT14S1SH-4S22Q contained a modified STII SD sequence and a gene encoding MST4/hGH fusion protein in which the 4th and 22nd amino acids of STII were replaced with Ser and Gln, respectively.

E. coli BL21 (DE3) was transformed with vector pT14S1SH-4S22Q. to obtain a transformant designated E. coli HM10014.

EXAMPLE 5

Construction of Vector Containing a Gene Encoding MST5/hGH Fusion Protein

The procedure of Step 2 of Example 1 was repeated except for using vector pT14SSH-4S obtained in Example 4 and the primers S7 and AS7 as used in Example 2, to obtain vector pT14SSH-4S20V22Q.

Then, the procedure of Step 3 of Example 1 was repeated using vector pT14SSH-4S20V22Q, to obtain vector pT14S1SH-4S20V22Q. Vector pT14S1SH-4S20V22Q contained a modified STII SD sequence and a gene encoding MST5/hGH fusion protein in which the 4th, 20th and 22nd amino acids of STII were replaced with Ser, Val and Gln, respectively.

E. coli BL21 (DE3) was transformed with vector pT14S1SH-4S20V22Q to obtain a transformant designated E. coli HM10015.

EXAMPLE 6

Construction of Vector Containing a Gene Encoding MST6/hGH Fusion Protein

Vector pT14SSH-4T20V22Q obtained in Example 2 was subjected to PCR using the following complementary primers S10 and AS10 which were designed to substitute Gly codon (GGT) for the 12th codon (ATG) of STII, to obtain vector pT14SSH-4T12G20V22Q.

sense primer S10(SEQ ID NO: 35): 5'-GCATTT CTTCTTGCATCTGGTTTCGTTTTTTCTATTGC-3' antisense primer AS10 (SEQ ID NO: 36): 5'-GCAATA GAAAAAACGAAACCAGATGCAAGAAGAAA TGC-3'

Then, the procedure of Step 3 of Example 1 was repeated using vector pT14SSH-4T12G20V22Q, to obtain vector pT14S1SH-4T12G20V22Q. Vector pT14S1SH-4T12G20V22Q contained a modified STII SD sequence and a gene encoding MST6/hGH fusion protein in which the 4th, 12th, 20th and 22nd amino acids of STII were replaced with Thr, Gly, Val and Gln, respectively.

E. coli BL21(DE3) was transformedwith vector pT14S1SH-4T12G20V22Q to obtain a transformant designated E. coli HM10016.

EXAMPLE 7

Construction of Vector Containing a Gene Encoding MST7/hGH Fusion Protein

Vector pT14SSH-4T12G20V22Q obtained in Example 6 was subjected to PCR using the following complementary primers S11 and AS11 which were designed to substitute Leu codon (CTT) for the 12th codon (GGT) of MST6, to obtain vector pT14SSH-4T12L20V22Q.

sense primer S11 (SEQ ID NO: 37): 5'-GCATTT CTTCTTGCATCTCTTTTCGTTTTTTCTATTGC-3' antisense primer AS11 (SEQ ID NO: 38): 5'-GCAATA GAA AAAACGAAAAGAGATGCAAGAAGAAA TGC-3'

Then, the procedure of Step 3 of Example 1 was repeated using vector pT14SSH-4T12L20V22Q, to obtain vector pT14S1SH-4T12L20V22Q. Vector pT14S1SH-4T12L20V22Q contained a modified STII SD sequence and a gene encoding MST7/hGH fusion protein in which the 4th, 12th, 20th and 22nd amino acids of STII were replaced with Thr, Leu, Val and Gln, respectively.

E. coli BL21(DE3) was transformed with vector pT14SSH-4T12L20V22Q to obtain a transformant designated E. coli HM10017.

EXAMPLE 8

Construction of Vector Containing a Gene Encoding MST8/hGH Fusion Protein

The procedure of Step 1 of Example 1 was repeated except for using the following complementary primers S12 and AS12 which were designed to substitute Lys and Ser codons (AAG and TCT) for the 4th and 5th codons (AAT and ATC) of STII, respectively, to obtain vector pT14SSH-4K5S.

sense primer S12 (SEQ ID NO: 39): 5'-GAGGTGTTT TATGAAAAAGAAGTCTGCATTTCTTC-3' antisense primer AS12 (SEQ ID NO: 40): 5-GAAGAA ATGCAGACTTCTTTTTCATAAAACACCTC-3'

Using vector pT14SSH-4K5S, the procedure of Step 2 of Example 1 was repeated to obtain vector pT14SSH-4K5S22Q. Vector pT14SSH-4K5S22Q contained a gene encoding MST8/hGH fusion protein in which the 4th, 5th and 22nd amino acids of STII were replaced with Lys, Ser and Gln, respectively.

E. coli BL21(DE3) was transformed with vector pT14SSH-4K5S22Q to obtain a transformant designated E. coli HM10018.

EXAMPLE 9

Construction of Vector Containing a Gene Encoding MST9/hGH Fusion Protein

The procedure of Step 1 of Example 1 was repeated except for using the following complementary primers S13 and AS13 which were designed to substitute Val, Lys and Thr codons (GTT, AAG and ACA) for the 2nd, 4th and 5th codons (AAA, AAT and ATC) of STII, respectively, to obtain vector pT14SSH-2V4K5T.

sense primer S13(SEQ ID NO: 41): 5'-GAGGTGTTT TATGGTTAAGAAGACAGCATTTCTTC-3' antisense primer AS13(SEQ ID NO: 42): 5'-GAAGAA ATGCTGTCTTCTTAACCATAAAACACCTC-3'

Using vector pT14SSH-2V4K5T, the procedure of Step 2 of Example 1 was repeated to obtain vector pT14SSH-2V4K5T22Q. Vector pT14SSH-2V4K5T22Q contained a gene encoding MST9/hGH fusion protein in which 2nd, 4th, 5th and 22nd amino acids of STII were replaced with Val, Lys, Thr and Gln, respectively.

E. coli BL21(DE3) was transformed with vector pT14SSH-2V4K5T22Q to obtain a transformant designated E. coli HM10019.

EXAMPLE 10

Construction of Vector Containing a Gene Encoding MST10/hGH Fusion Protein

The procedure of Step 1 of Example 1 was repeated except for using the following complementary primers S14 and AS14 which were designed to substitute Lys codon (AAG) for the 4th codon (AAT) of STII, to obtain vector pT14SSH-4K.

sense primer S14(SEQ ID NO: 43): 5'-GAGGTG TTTTATGAAAAAGAAGATCGCATTTCTTC-3' antisense primer AS14(SEQ ID NO: 44): 5'-GAAGAA ATGCGATCTTCTTTTTCATAAAACACCTC-3'

Using vector pT14SSH-4K was used, the procedure of Step 2 of Example 1 was repeated to obtain vector pT14SSH-4K22Q.

Vector pT14SSH-4K22Q was subjected to PCR using the primers S7 and AS7 employed in Example 2 to obtain vector pT14SSH-4K20V22Q. Vector pT14SSH-4K20V22Q contained a gene encoding MST10/hGH fusion protein in which the 4th, 20th and 22nd amino acids of STII were replaced with Lys, Val and Gln, respectively.

E. coli BL21(DE3) was transformed with vector pT14SSH-4K20V22Q to obtain a transformant designated E. coli HM10020.

EXAMPLE 11

Production of hGH Using MST/hGH Gene

To examine the effect of MST on the production of hGH, the procedure of Preparation Example 4 was repeated using the transformants (E. coli HM10011 to HM10020) prepared in Examples 1 to 10, in the absence of added IPTG. Transformant HM10010 prepared in Step 3 of Preparation Example 3 was used as a control. The hGH level was calculated as the amount of hGH produced per 1 l of culture media. The results are shown in Table III.

TABLE III

| Transformant | Expression Vector | hGH Level (mg/l) |
|---|---|---|
| E. coli HM10010 | P14SSH | 330 |
| E. coli HM10012 | pT14S1SH-4T20V22Q | 1,300 |
| E. coli HM10013 | pT14S1SH-4K5T22Q | 1,270 |
| E. coli HM10014 | pT14S1SH-4S22Q | 1,320 |
| E. coli HM10015 | pT14S1SH-4S20V22Q | 1,230 |
| E. coli HM10016 | pT14S1SH-4T12G20V22Q | 1,173 |
| E. coli HM10017 | pT14S1SH-4T12L20V22Q | 1,282 |
| E. coli HM10018 | pT14SSH-4K5S22Q | 1,150 |
| E. coli HM10019 | pT14SSH-2V4K5T22Q | 1,140 |
| E. coli HM10020 | pT14SSH-4K20V22Q | 1,230 |

As can be seen from Table III, each of the vectors of the present invention containing an MST gene produces hGH in a higher yield than the control vector p14SSH containing native STII. Further, among the vectors of the present invention, those containing modified STII SD sequences lead to a high level of hGH as compared to the vectors containing the native STII SD sequence.

EXAMPLE 12

Purification of hGH

Transformant *E. coli* HM10011 prepared in Example 1, was cultured in LB medium while the expression of MST/hGH gene was induced using IPTG, and the culture was centrifuged for 6,000 rpm for 20 min. to harvest cells. The periplasmic solution was prepared from the cells by repeating the procedure of Preparation Example 4.

The periplasmic solution was adjusted to pH 5.3 to 6.0, adsorbed on DEAE-Separose (Pharmacia Inc., Sweden) column pre-equilibrated to pH 5.8, and then, the column was washed with 10 mM NaCl solution. hGH was eluted using buffer solutions containing 20 mM, 40 mM and 80 mM NaCl, respectively, and fractions containing hGH collected and combined.

The combined fractions were subjected to Phenyl Separose (Pharmacia Inc., Sweden) column chromatography to obtain hGH having a purity of 99%, which was further purified by Sephadex G-100(Pharmacia Inc., Sweden) column chromatography.

The purified hGH fraction was subjected to sodium dodecylsulfate polyacrylamide gel electrophoresis (SDS-PAGE) to determine the purity and approximate concentration of the hGH, and then subjected to ELISA to determine the exact hGH concentration in this fraction.

Figure 5:
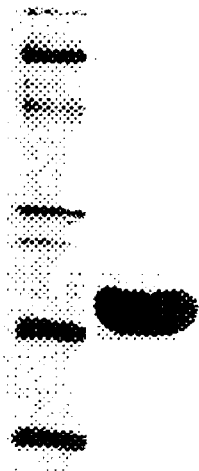
FIG. 5 reproduces the result of SDS-PAGE analysis of purified hGH.

FIG. 5 reproduces the result of SDS-PAGE wherein lane 1 shows protein size marker proteins; and lane 2, the purified hGH. As can be seen from FIG. 5, high level of pure hGH is obtained by culturing the transformant of the present invention.

Further, the N-terminal amino acid sequence of hGH was determined and the result shows that hGH produced according to the present invention is not methionylated at N-terminus.

While the invention has been described with respect to the above specific embodiments, it should be recognized that various modifications and changes may be made to the invention by those skilled in the art which also fall within the scope of the invention as defined by the appended claims.

WO 00/15661   PCT/KR99/00547

- 29 -

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

To. Hanmi Pharm. Co., Ltd.

893-5 Hajeo-ri Paltan-myun
Hwasung-Kun
Kyonggi-do, Korea

RECEIPT IN THE CASE OF AN ORIGINAL
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR : <br><br> HM10011 | Accession number given by the INTERNATIONAL DEPOSITARY AUTHORITY: <br><br> KCCM-10137 |
| II. SCIENTIFIC DESCRIPTION AND/OR PROPOSED TAXONOMIC DESIGNATION | |
| The microorganism identified under I above was accompanied by: <br> ☐ a scientific description <br> ☐ a proposed taxonomic designation <br> (Mark with a cross where applicable) | |
| III. RECEIPT AND ACCEPTANCE | |
| This International Depositary Authouity accepts the microorganism identified under I above, which was received by it on Aug. 12. 1998 (date of the original deposit)[1] | |
| IV. INTERNATIONAL DEPOSITARY AUTHORITY | |
| Name : Korean Culture Center of Microorganisms <br><br> Address : Department of Food Engineering <br> College of Eng. Yonsei University <br> Sodaemun-gu, Seoul 120-749 <br> Korea | Signature(s) of person(s) having the power to represent the International Depositary Authority of of authouized official(s) <br><br> Date: Aug. 22. 1998 |

[1] Where Rule 6.4(d) applies, such date is the date on which the status of international depositary authority was acquired : where a deposit made outside the Budapest Treaty after the acquisition of the status of international depositary authority is converted into a deposit under the Budapest Treaty, such date is the date on which the microorganism was received by the international depositary authouity.

Form BP/4 (KCCM Form 17)                                                    Sole page WO 00/15661                                                              PCT/KR99/00547

- 30 -

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

To. Hanmi Pharm. Co., Ltd.

893-5 Hajeo-ri Paltan-myun
Hwasung-Kun
Kyonggi-do, Korea

RECEIPT IN THE CASE OF AN ORIGINAL
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR : <br><br> HM10012 | Accession number given by the INTERNATIONAL DEPOSITARY AUTHORITY: <br><br> KCCM-10138 |
| II. SCIENTIFIC DESCRIPTION AND/OR PROPOSED TAXONOMIC DESIGNATION | |
| The microorganism identified under I above was accompanied by: <br> ☐ a scientific description <br> ☐ a proposed taxonomic designation <br> (Mark with a cross where applicable) | |
| III. RECEIPT AND ACCEPTANCE | |
| This International Depositary Authouity accepts the microorganism identified under I above, which was received by it on Aug. 12. 1998 (date of the original deposit)[1] | |
| IV. INTERNATIONAL DEPOSITARY AUTHORITY | |
| Name : Korean Culture Center of Microorganisms <br><br> Address : Department of Food Engineering <br> College of Eng. Yonsei University <br> Sodaemun-gu, Seoul 120-749 <br> Korea | Signature(s) of person(s) having the power to represent the International Depositary Authority of of authouized official <br><br> Date: Aug. 22. 1998 |

[1] Where Rule 6.4(d) applies, such date is the date on which the status of international depositary authority was acquired : where a deposit made outside the Budapest Treaty after the acquisition of the status of international depositary authority is converted into a deposit under the Budapest Treaty, such date is the date on which the microorganism was received by the international depositary authouity.

Form BP/4 (KCCM Form 17)                                                                    Sole page

What is claimed is:

1. A modified *E coli* enterotoxin II signal peptide, wherein the 4th and the 22nd amino acids of the *E coli* enterotoxin II signal peptide having the amino acid sequence of SEQ ID NO: 1 are replaced by Thr and Gln, respectively.

2. The modified *E. coli* enterotoxin II signal peptide of claim 1, wherein the 20th amino acid is further replaced by Val.

3. The modified *E. coli* enterotoxin II signal peptide of claim 1, wherein the 12th and the 20th amino acids are further replaced by Gly and Val, respectively.

4. The modified *E. coli* enterotoxin II signal peptide of claim 1, wherein the 12th and the 20th amino acids are further replaced by Leu and Val, respectively.

* * * * *

SEQUENCE LISTING

<160> NUMBER OF SEQ ID NOS: 44

<210> SEQ ID NO 1
<211> LENGTH: 23
<212> TYPE: PRT
<213> ORGANISM: Escherichia coli
<220> FEATURE:
<221> NAME/KEY: SIGNAL
<222> LOCATION: (1)..(23)
<223> OTHER INFORMATION: E. coli enterotoxin II signal peptide

<400> SEQUENCE: 1

Met Lys Lys Asn Ile Ala Phe Leu Leu Ala Ser Met Phe Val Phe Ser
 1               5                  10                  15

Ile Ala Thr Asn Ala Tyr Ala
            20

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: a modified
      E. coli enterotoxin II Shine-Dalgano sequence

<400> SEQUENCE: 2
gaggtgtttt                                                                  10

<210> SEQ ID NO 3
<211> LENGTH: 35
<212> TYPE: DNA
<213> ORGANISM: Escherichia coli
<220> FEATURE:
<221> NAME/KEY: RBS
<222> LOCATION: (1)..(35)
<223> OTHER INFORMATION: E. coli enterotoxin II Shine-Dalgano sequence

<400> SEQUENCE: 3
gctctagagg ttgaggtgtt ttatgaaaaa gaata                                      35

<210> SEQ ID NO 4
<211> LENGTH: 8
<212> TYPE: PRT
<213> ORGANISM: Homo sapiens
<220> FEATURE:
<221> NAME/KEY: PEPTIDE
<222> LOCATION: (1)..(8)
<223> OTHER INFORMATION: an N-terminal portion of human growth hormone

<400> SEQUENCE: 4

Phe Pro Thr Ile Pro Leu Ser Arg
 1               5

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:
      oligonucleotide probe synthesized based on the
      amino acid sequence for the N-terminal portion of
      human growth hormone

<400> SEQUENCE: 5
ttcccaacca ttcccttatc cagg                                                  24

```
<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: sense
      primer S1

<400> SEQUENCE: 6
ccgcatatgt tcccaaccat tccc                                          24

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: antisense
      primer AS1

<400> SEQUENCE: 7
gctggatcct agaagccaca gctgc                                         25

<210> SEQ ID NO 8
<211> LENGTH: 72
<212> TYPE: DNA
<213> ORGANISM: Artificial Sequence
<220> FEATURE:
<223> OTHER INFORMATION: Description of Artificial Sequence: sense
      strand oligonucleotide STII S1

<400> SEQUENCE: 8
tcatgaaaaa gaatatcgca tttcttcttg catctatgtt cgttttttct attgctacaa   60
atgcctacgc gt                                                       72

<210> SEQ ID NO 9
<211> LENGTH: 72
<212> TYPE: DNA
<213> ORGANISM: Artificial Sequence
<220> FEATURE:
<223> OTHER INFORMATION: Description of Artificial Sequence: antisense
      strand oligonucleotide STII AS1

<400> SEQUENCE: 9
acgcgtaggc atttgtagca atagaaaaaa cgaacataga tgcaagaaga aatgcgatat   60 tcttttttcat ga                                                      72

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: sense
      primer S2

<400> SEQUENCE: 10
gcgacgcgtt cccaaccatt cccttatcc                                     29

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: sense
      primer S3

<400> SEQUENCE: 11
```

```
gctctagagg ttgaggtgat tttatgaaaa agaata                                36
```

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: antisense
      primer AS3

<400> SEQUENCE: 12

```
ggatgccacg ctggatccta gaaagccaca gctgc                                 35
```

<210> SEQ ID NO 13
<211> LENGTH: 23
<212> TYPE: PRT
<213> ORGANISM: Artificial Sequence
<220> FEATURE:
<223> OTHER INFORMATION: Description of Artificial Sequence: MST1

<400> SEQUENCE: 13

Met Lys Lys Thr Ile Ala Phe Leu Leu Ala Ser Met Phe Val Phe Ser
 1               5                  10                  15

Ile Ala Thr Asn Ala Gln Ala
            20

<210> SEQ ID NO 14
<211> LENGTH: 23
<212> TYPE: PRT
<213> ORGANISM: Artificial Sequence
<220> FEATURE:
<223> OTHER INFORMATION: Description of Artificial Sequence: MST2

<400> SEQUENCE: 14

Met Lys Lys Thr Ile Ala Phe Leu Leu Ala Ser Met Phe Val Phe Ser
 1               5                  10                  15

Ile Ala Thr Val Ala Gln Ala
            20

<210> SEQ ID NO 15
<211> LENGTH: 23
<212> TYPE: PRT
<213> ORGANISM: Artificial Sequence
<220> FEATURE:
<223> OTHER INFORMATION: Description of Artificial Sequence: MST3

<400> SEQUENCE: 15

Met Lys Lys Lys Thr Ala Phe Leu Leu Ala Ser Met Phe Val Phe Ser
 1               5                  10                  15

Ile Ala Thr Asn Ala Gln Ala
            20

<210> SEQ ID NO 16
<211> LENGTH: 23
<212> TYPE: PRT
<213> ORGANISM: Artificial Sequence
<220> FEATURE:
<223> OTHER INFORMATION: Description of Artificial Sequence: MST4

<400> SEQUENCE: 16

Met Lys Lys Ser Ile Ala Phe Leu Leu Ala Ser Met Phe Val Phe Ser
 1               5                  10                  15

Ile Ala Thr Asn Ala Gln Ala
            20

```
<210> SEQ ID NO 17
<211> LENGTH: 23
<212> TYPE: PRT
<213> ORGANISM: Artificial Sequence
<220> FEATURE:
<223> OTHER INFORMATION: Description of Artificial Sequence: MST5

<400> SEQUENCE: 17

Met Lys Lys Ser Ile Ala Phe Leu Leu Ala Ser Met Phe Val Phe Ser
 1               5                  10                  15

Ile Ala Thr Val Ala Gln Ala
            20

<210> SEQ ID NO 18
<211> LENGTH: 23
<212> TYPE: PRT
<213> ORGANISM: Artificial Sequence
<220> FEATURE:
<223> OTHER INFORMATION: Description of Artificial Sequence: MST6

<400> SEQUENCE: 18

Met Lys Lys Thr Ile Ala Phe Leu Leu Ala Ser Gly Phe Val Phe Ser
 1               5                  10                  15

Ile Ala Thr Val Ala Gln Ala
            20

<210> SEQ ID NO 19
<211> LENGTH: 23
<212> TYPE: PRT
<213> ORGANISM: Artificial Sequence
<220> FEATURE:
<223> OTHER INFORMATION: Description of Artificial Sequence: MST7

<400> SEQUENCE: 19

Met Lys Lys Thr Ile Ala Phe Leu Leu Ala Ser Leu Phe Val Phe Ser
 1               5                  10                  15

Ile Ala Thr Val Ala Gln Ala
            20

<210> SEQ ID NO 20
<211> LENGTH: 23
<212> TYPE: PRT
<213> ORGANISM: Artificial Sequence
<220> FEATURE:
<223> OTHER INFORMATION: Description of Artificial Sequence: MST8

<400> SEQUENCE: 20

Met Lys Lys Lys Ser Ala Phe Leu Leu Ala Ser Met Phe Val Phe Ser
 1               5                  10                  15

Ile Ala Thr Asn Ala Gln Ala
            20

<210> SEQ ID NO 21
<211> LENGTH: 23
<212> TYPE: PRT
<213> ORGANISM: Artificial Sequence
<220> FEATURE:
<223> OTHER INFORMATION: Description of Artificial Sequence: MST9

<400> SEQUENCE: 21

Met Val Lys Lys Thr Ala Phe Leu Leu Ala Ser Met Phe Val Phe Ser
 1               5                  10                  15

Ile Ala Thr Asn Ala Gln Ala
```

<210> SEQ ID NO 22
<211> LENGTH: 23
<212> TYPE: PRT
<213> ORGANISM: Artificial Sequence
<220> FEATURE:
<223> OTHER INFORMATION: Description of Artificial Sequence: MST10

<400> SEQUENCE: 22

Met Lys Lys Lys Ile Ala Phe Leu Leu Ala Ser Met Phe Val Phe Ser
 1               5                  10                  15

Ile Ala Thr Val Ala Gln Ala
            20

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: sense
      primer S4

<400> SEQUENCE: 23
ggtgttttat gaaaaagaca atcgcatttc ttc                                33

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: antisense
      primer AS4

<400> SEQUENCE: 24
gaagaaatgc gattgtcttt ttcataaaac acc                                33

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: sense
      primer S5

<400> SEQUENCE: 25
caaatgccca agcgttccca                                               20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: antisense
      primer AS5

<400> SEQUENCE: 26
tgggaacgct tgggcatttg                                               20

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: sense
      primer S6

<400> SEQUENCE: 27
tctagaggtt gaggtgtttt atga                                    24

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: antisense
      primer AS6

<400> SEQUENCE: 28
tcataaaaca cctcaacctc taga                                    24

<210> SEQ ID NO 29
<211> LENGTH: 45
<212> TYPE: DNA
<213> ORGANISM: Artificial Sequence
<220> FEATURE:
<223> OTHER INFORMATION: Description of Artificial Sequence: sense
      primer S7

<400> SEQUENCE: 29 gtttttcta ttgctacagt tgcccaagcg ttcccaacca ttccc              45

<210> SEQ ID NO 30
<211> LENGTH: 45
<212> TYPE: DNA
<213> ORGANISM: Artificial Sequence
<220> FEATURE:
<223> OTHER INFORMATION: Description of Artificial Sequence: antisense
      primer AS7

<400> SEQUENCE: 30
gggaatggtt gggaacgctt gggcaactgt agcaatagaa aaaac             45

<210> SEQ ID NO 31
<211> LENGTH: 35
<212> TYPE: DNA
<213> ORGANISM: Artificial Sequence
<220> FEATURE:
<223> OTHER INFORMATION: Description of Artificial Sequence: sense
      primer S8

<400> SEQUENCE: 31
gaggtgtttt atgaaaaaga agacagcatt tcttc                        35

<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence: antisense
      primer AS8

<400> SEQUENCE: 32
gaagaaatgc tgtcttcttt ttcataaaac acctc                        35

<210> SEQ ID NO 33
<211> LENGTH: 35
<212> TYPE: DNA
<213> ORGANISM: Artificial Sequence
<220> FEATURE:
<223> OTHER INFORMATION: Description of Artificial Sequence: sense
      primer S9

<400> SEQUENCE: 33

```
gaggtgtttt atgaaaaagt ctatcgcatt tcttc                              35
```

<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence: antisense
      primer AS9

<400> SEQUENCE: 34

```
gaagaaatgc gatagacttt ttcataaaac acctc                              35
```

<210> SEQ ID NO 35
<211> LENGTH: 38
<212> TYPE: DNA
<213> ORGANISM: Artificial Sequence
<220> FEATURE:
<223> OTHER INFORMATION: Description of Artificial Sequence: sense
      primer S10

<400> SEQUENCE: 35

```
gcatttcttc ttgcatctgg tttcgttttt tctattgc                           38
```

<210> SEQ ID NO 36
<211> LENGTH: 38
<212> TYPE: DNA
<213> ORGANISM: Artificial Sequence
<220> FEATURE:
<223> OTHER INFORMATION: Description of Artificial Sequence: antisense
      primer AS10

<400> SEQUENCE: 36

```
gcaatagaaa aaacgaaacc agatgcaaga agaaatgc                           38
```

<210> SEQ ID NO 37
<211> LENGTH: 38
<212> TYPE: DNA
<213> ORGANISM: Artificial Sequence
<220> FEATURE:
<223> OTHER INFORMATION: Description of Artificial Sequence: sense
      primer S11

<400> SEQUENCE: 37

```
gcatttcttc ttgcatctct tttcgttttt tctattgc                           38
```

<210> SEQ ID NO 38
<211> LENGTH: 38
<212> TYPE: DNA
<213> ORGANISM: Artificial Sequence
<220> FEATURE:
<223> OTHER INFORMATION: Description of Artificial Sequence: antisense
      primer AS11

<400> SEQUENCE: 38

```
gcaatagaaa aaacgaaaag agatgcaaga agaaatgc                           38
```

<210> SEQ ID NO 39
<211> LENGTH: 35
<212> TYPE: DNA
<213> ORGANISM: Artificial Sequence
<220> FEATURE:
<223> OTHER INFORMATION: Description of Artificial Sequence: sense
      primer S12

<400> SEQUENCE: 39

```
gaggtgtttt atgaaaaaga agtctgcatt tcttc                               35
```

<210> SEQ ID NO 40
<211> LENGTH: 35
<212> TYPE: DNA
<213> ORGANISM: Artificial Sequence
<220> FEATURE:
<223> OTHER INFORMATION: Description of Artificial Sequence: antisense
      primer AS12

<400> SEQUENCE: 40

```
gaagaaatgc agacttcttt ttcataaaac acctc                               35
```

<210> SEQ ID NO 41
<211> LENGTH: 35
<212> TYPE: DNA
<213> ORGANISM: Artificial Sequence
<220> FEATURE:
<223> OTHER INFORMATION: Description of Artificial Sequence: sense
      primer S13

<400> SEQUENCE: 41

```
gaggtgtttt atggttaaga agacagcatt tcttc                               35
```

<210> SEQ ID NO 42
<211> LENGTH: 35
<212> TYPE: DNA
<213> ORGANISM: Artificial Sequence
<220> FEATURE:
<223> OTHER INFORMATION: Description of Artificial Sequence: antisense
      primer AS13

<400> SEQUENCE: 42

```
gaagaaatgc tgtcttctta accataaaac acctc                               35
```

<210> SEQ ID NO 43
<211> LENGTH: 35
<212> TYPE: DNA
<213> ORGANISM: Artificial Sequence
<220> FEATURE:
<223> OTHER INFORMATION: Description of Artificial Sequence: sense
      primer S14

<400> SEQUENCE: 43

```
gaggtgtttt atgaaaaaga agatcgcatt tcttc                               35
```

<210> SEQ ID NO 44
<211> LENGTH: 35
<212> TYPE: DNA
<213> ORGANISM: Artificial Sequence
<220> FEATURE:
<223> OTHER INFORMATION: Description of Artificial Sequence: antisense
      primer AS14

<400> SEQUENCE: 44

```
gaagaaatgc gatcttcttt ttcataaaac acctc                               35
```